United States Patent
Goletz et al.

(10) Patent No.: US 8,741,365 B2
(45) Date of Patent: Jun. 3, 2014

(54) FERMENTATION PROCESS

(75) Inventors: Steffen Goletz, Glienicke (DE); Philippe Ulsemer, Schildow (DE)

(73) Assignee: Glycotope GmbH, Berlin (DE)

( * ) Notice: Subject to any disclaimer, the term of this patent is extended or adjusted under 35 U.S.C. 154(b) by 547 days.

(21) Appl. No.: 12/991,827

(22) PCT Filed: May 13, 2009

(86) PCT No.: PCT/EP2009/003401
§ 371 (c)(1),
(2), (4) Date: Jan. 28, 2011

(87) PCT Pub. No.: WO2009/138220
PCT Pub. Date: Nov. 19, 2009

(65) Prior Publication Data
US 2011/0129570 A1    Jun. 2, 2011

Related U.S. Application Data

(60) Provisional application No. 61/052,788, filed on May 13, 2008.

(30) Foreign Application Priority Data

May 13, 2008 (EP) .................................... 08008873
Nov. 20, 2008 (EP) .................................... 08020217

(51) Int. Cl.
| | |
|---|---|
| A23C 9/12 | (2006.01) |
| A23C 9/127 | (2006.01) |
| C12N 1/20 | (2006.01) |
| C12P 39/00 | (2006.01) |
| C12P 7/56 | (2006.01) |
| A23B 4/12 | (2006.01) |

(52) U.S. Cl.
USPC ...... 426/34; 426/7; 426/61; 435/42; 435/139; 435/252.1

(58) Field of Classification Search
USPC .................. 426/7, 34, 61; 435/42, 139, 252.1
See application file for complete search history.

(56) References Cited

U.S. PATENT DOCUMENTS

2004/0029127 A1    2/2004  Postaire et al.
2004/0115177 A1*   6/2004  Harris et al. ............... 424/93.45

FOREIGN PATENT DOCUMENTS

| EP | 1 371 735 | 12/2003 |
|---|---|---|
| EP | 1 920 781 | 5/2008 |
| WO | WO 00/41576 | 7/2000 |
| WO | 2005/003773 A1 | 1/2005 |
| WO | WO 2007/124992 | 11/2007 |
| WO | WO 2008/055702 | 5/2008 |

OTHER PUBLICATIONS

Hargrove et al. 1980. Growth Response of Weanling Rats to Heated, Aged, Fractionated, and Chemically Treated Yogurts. Journal of Dairy Science, vol. 63, pp. 1065-1072.*
Marshall, VM "Gut-Derived Organisms for Milk Fermentation," Journal of Chemical Technology and Biotechnology, 51(4): 548-553 (1991).
Riemer AB et al. "Induction of IgG antibodies against the GD2 carbohydrate tumor antigen by vaccination with peptide mimotopes," European Journal of Immunology, 36(5): 1267-1274 (2006).
Office Action for European Patent Application No. 09 745 554.7 dated Jul. 20, 2011.
International Search Report for International Application No. PCT/EP2009/003401, dated Sep. 10, 2009.
U.S. Appl. No. 12/514,248, filed Nov. 25, 2009, Steffen Goletz.
U.S. Appl. No. 10/589,447, filed Feb. 7, 2008, Steffen Goletz.
U.S. Appl. No. 12/514,248, filed Nov. 25, 2009, Steffen Goletz, Office Action Mailed Apr. 11, 2013.
U.S. Appl. No. 12/514,248, filed Nov. 25, 2009, Steffen Goletz, Office Action Mailed Sep. 21, 2012.
U.S. Appl. No. 10/589,447, filed Feb. 7, 2008, Steffen Goletz, Office Action Mailed Feb. 25, 2013.
U.S. Appl. No. 10/589,447, filed Feb. 7, 2008, Steffen Goletz, Office Action Mailed Aug. 3, 2010.
Raska, Milan et al., "Glycosylation patterns of HIV-1 gp120 Depends on he Type of Expressing Cells and Affect Anitbody Recognition," The Journal of Biological Chemistry, vol. 285(27):20860-20869 (2010).

* cited by examiner

Primary Examiner — Jon P Weber
Assistant Examiner — Kailash C Srivastava
(74) Attorney, Agent, or Firm — Nelson Mullins Riley & Scarborough LLP; Jane E. Remillard, Esq.; Jill Gorny Sloper, Esq.

(57) ABSTRACT

The present disclosure relates in one embodiment to a method of producing a fermented food, wherein a raw food material is combined with a starter culture for fermentation, wherein at least one microorganism of the genus *Bacteroides* and/or at least one microorganism having at least a cell surface structure which corresponds to a human carbohydrate structure is added. Further disclosed are processing aids and fermented foods containing respective microorganisms.

10 Claims, 3 Drawing Sheets

Fig. 1

Galβ1-3GalNAcα1-O-P

FERMENTATION PROCESS

This application is a national stage filing under 35 U.S.C. §371 of International Application No. PCT/EP2009/003401 filed on 13 May 2009, which claims priority of European Patent Application No. 08008873.5, filed on 13 May 2008, and U.S. Provisional Application No. 61/052,788, filed on 13 May 2008, and European Patent Application No. 08020217.9, filed on 20 Nov. 2008. The contents of all four applications are incorporated herein by reference.

The present invention relates to a method of producing fermented food as well as suitable processing aids to render the production of a fermented food possible. Furthermore, fermented foods are made available.

Fermented foodstuffs, such as for example yogurt, cheese, raw sausage, and vegetables that are fermented acidly, are an integral component of our nutrition. Various methods are used for producing fermented foods. Traditional fermentation methods are based, for example, on spontaneous fermentation (cacao, coffee, for example) or are triggered through addition of microorganisms (alcoholic fermentation, acetic fermentation, and lactic fermentation, for example). Current fermentation methods are based on the addition of starter cultures to the respective raw food material (for example milk to produce yogurt or cheese). Starter cultures afford various benefits as opposed to traditional production processes. For one, economical losses are prevented as a result of fewer defective productions and shortening of production processes. Furthermore, the raw materials can normally react better. As also a mixture of various starter cultures can be utilized, oftentimes the results with respect to taste, safety, and homogeneity, are better. Products can be produced which otherwise would not be possible without targeted intervention in the production process. All microorganisms are normally killed in the raw material before the starter cultures are added, for example through pasteurization.

An essential objective for developing and improving known fermentation processes is the development and selection of appropriate microorganisms for the fermentation process because they decisively influence the fermentation process. The metabolic activity of used microorganism is determinative, for example, for the aroma, the acidification degree and/or color of the finished product.

Furthermore, microorganisms have a great potential for the field of nutrition when positively affecting the health condition or the metabolism. A known example of fermented foods that positively affect the health of the consumer involves probiotic foodstuffs. A probiotic is a preparation of viable microorganisms which, when consumed in sufficient amounts, have a health-promoting influence on the consumer. Probiotic lactic acid bacteria are used the longest, although yeasts and other species are in use as well. After originally primary probiotic yogurt products have been offered, other foods, such as, for example, quark, cheese or sausage, which contain probiotic bacteria, are on the market for some time. Probiotic products, such as, for example, yogurt, can be produced in various ways. Normally, the yogurt is at first produced in a conventional manner through addition of typical starter cultures, and then the probiotic bacterial strain is admixed to the fermented product. Depending on the bacterial strain used, fermentation of milk may also be realized by the probiotic bacterial strain itself; the product contains in this case exclusively the probiotic bacterial strain.

There is a great need for providing further microorganisms which can be used either instead of or in combination with known microorganisms for production of fermented foods.

The present invention is therefore based on the object to provide appropriate microorganisms for production of fermented foods.

This object is attained by a method for production of fermented foods, wherein a raw food material is combined with a starter culture for fermentation. The method according to the invention is characterized in that at least one microorganism is added having at least one cell surface structure which corresponds to a human carbohydrate structure, in particular a human carbohydrate antigen.

Carbohydrates are important cell markers which are characteristic for various cell types and tissues. Certain carbohydrate structures—also called carbohydrate antigens—are oftentimes encountered in combination with diseases. For example, an abnormal glycosylation is a typical characteristic of cancer cells. These abnormal carbohydrate structures are hardly present or not present at all on healthy human cells, but are present only when the cells undergo a pathological change. They are thus characteristic markers (antigens) for pathologically altered cells. There are thus efforts in the state of the art to produce vaccines based on carbohydrate antigens. Carbohydrate structures are however only poorly immunogenic and thus not necessary suitable to trigger a sufficient immune response. An effective immune response is however essential to, for example, buildup a protective effect against the respective carbohydrate structure antigen. When the immune system contacts for the first time the respective carbohydrate antigen and forms an immune response, the organism would be more capable as a result of the immunization to react when the respective carbohydrate structure (in a cancer cell for example) is again present and triggers an immune defense accordingly. It is therefore advantageous if an effective immune response, which is specific to the carbohydrate structure, can be triggered. Corresponding health-promoting effects can be realized with microorganisms according to the invention because they are sufficiently immunogenic and have at least one cell surface structure which corresponds to a human carbohydrate structure. Furthermore, these microorganisms may be used advantageously as processing aid, i.e., for example, as starter culture or as additive that can be e.g. used after fermentation during production of fermented foods.

According to one embodiment, the human carbohydrate structure is a disease-specific antigen, in particular a tumor-associated antigen. The cell surface structure of the microorganism may have, respectively carry in accordance with one embodiment the desired human carbohydrate structure. It is, however, sufficient, if the cell surface structure corresponds to the human carbohydrate structure but is not identical with it. Glycosylation in microorganisms fundamentally differs from glycosylation in humans or animals. Surprisingly, it has been found that microorganisms are capable to express "human" carbohydrate antigens as cell surface structure. These cell surface structures often differ in their structure from the actual human carbohydrate structure, but have, however, a basic structure which corresponds or is at least highly similar to the corresponding human carbohydrate structure in its structure/conformation. Such "corresponding" cell surface structures thus mimic the original human carbohydrate structure and are covered by the term "a cell surface structure which corresponds to a human carbohydrate structure". Such a cell surface structure which corresponds to a human carbohydrate structure may either also be a carbohydrate structure but also a polypeptide, peptide, lipid, or a combination thereof. What is important is that these cell surface structures have a conformation which corresponds to the corresponding human carbohydrate structure. The presence of such a cell surface structure can easily be tested for example through use of antibodies which specifically recognize the human carbohydrate structure and bind them accordingly. When the microorganism has a cell surface structure which corresponds to the desired human carbohydrate structure, it is also recognized by the antibody which specifically binds the human carbohydrate structure, and is respectively bound. In this way, it can be checked/analysed whether the microorganism has a cell surface structure which corresponds to a human carbohydrate structure. Furthermore, using a respective test, appropriate microorganisms which have the desired human carbohydrate structure or mimic such, can be identified or selected. Besides antibodies, also other binding molecules can be used which are capable to bind carbohydrate structures with sufficient specificity. Non-limiting examples include lectins and selectins.

The following tables 1 and 2 give an overview about important human disease-specific carbohydrate structures and disclose appropriate binders such as, for example, antibodies which permit selection and identification of a microorganism having at least one cell surface structure which corresponds to the listed human carbohydrate structure.

TABLE 1

| Disease | Carbohydrate Antigen |
| --- | --- |
| Melanoma | GM2, GD2, GD3L, GD3, 9-O-Acetyl GD2, 9-O-Acetyl GD3 |
| B cell lymphoma | GM2, GD2 |
| Small-cell lung cancer | GM2, Fucosyl GM1, Globo H, Polysialyic Acid, sLe a (Sialyl-Lewis a) |
| Breast cancer | GM2, Globo H, TF, Core-1, Galbeta1-3GalNAc-, Le y (Lewis-Y) |
| Prostate cancer | GM2, Globo H, Tn, sTn, TF, Le y, sLe a, Core-1 |
| Lung cancer | GM2 Globo H, Le y, Core-1 |
| Intestinal cancer | GM2, sTn, TF, Le y, Core-1, |
| Ovarian cancer | GM2, Globo H, sTn, TF, Le y, Core-1 |
| Stomach cancer | GM2, Le y, Le a, sLe a, Core-1 |
| Neuroblastoma | GM2, GD2, GD3L, Polysialic Acid |
| Sarcoma | GM2, GD2, GD3L, GD3 |
| Pancreatic cancer | sLe a, sLe x (Sialyl Lewis x) |
| Gatro-intestinal cancer | sLe a, sLe x |
| CD4 + CD56 + neoplasia | sLe x (CD15) |

TABLE 2

| Carbohydrate Structure | Molecules Binding Carbohydrate Structure | |
| --- | --- | --- |
| | Lectin | Monoclonal Antibody |
| TF or Core-1 | Galectin, C-typical Lectins of Macrophages, Sialoadhesin, PNA [3], Jacalin [3], MAL [3], EEL [3], ECL [3] | Nemod-TF1 [2], Nemod-TF21 [2], A78-G/A7 [2], HB-T1 [11], HH8 [14], A68-B/A11 [2] |
| Tn | Galectin, C-typical Lectins of Macrophages, Sialoadhesin, BPL [3], DBA [3], GSL I [3], MPL [3], RCA [3], SJS [3], SBA [3] | HB-T1 [11] |
| Sialyl-Tn | | CA 72-4 [1], TKH2 [1], HB-STn1 [11] |
| Globo-H | | A69-A/E8 [2], VK9 [13] |
| Lewis-Y | | A46-B/B10 [2], A63-D/B12 [2], A51-B/A6 [2], A70-C/C8 [2], A70-A/A9 [2], |
| Sialyl-Lewis-A | E-selectin | CA 195 [1], CA 50 [1], 121SLE [12] |
| Sialyl-Lewis-X | E-selectin | CA 19-9 [1], KM931 [10], T174 [10] |
| Lewis-X | | 73-30 [4], BG-7 (P12) [4] |
| Lewis-A | | CA 195 [1], MAB2108 (7LE) [4], BG-5 (T174) [4], PR5C5 [12] |
| Lewis-B | | MAB2102 (2.25LE) [4], BG-6 (T218) [4], |
| Sialylated type 1 chain | | CA 242 [1] |
| sLac | | CA 50 [1], DU-PAN-2 [1], |
| Polysialic acid | MAL II [3], SNA [3] | Mab735 [9], 5A5 [13] |
| Fucosyl GM1 | | F12 [13] |
| GM2 | | BP283 [5], PGNX [13] |
| GD2 | | Mab 126 [1], 3F8 [5], ME 36.1 [1] |
| GD3 | | R24 [6], MAB2053 [7], ME 36.1 [1] |
| 9-O-Acetyl GD2 | | 3F8 [8] |
| 9-O-Acetyl GD3 | | ME3.11 [1] |

[1] Orntoft et al. Electrophoresis 1999, 20, 362-371
[2] Glycotope GmbH Berlin, www.glycotope.com
[3] vector laboratories, www.vectorlabs.com
[4] Amano et al. Clin Diagn Lab Immunol 1997(Sep), 540-544
[5] Acris Antibodies GmbH, www.acris-antibodies.com
[6] Reaman et al. Cancer Res 1990 50 (1): 202-5
[7] CHEMICON International, Inc. www.chemicon.com
[8] Ye et al. 1992; 50 (2): 197-201
[9] Husmann et al. J Histochem Cytochem 1990; 38 (2): 209-15
[10] Calbiochem, www.Calbiochem.com
[11] DakoCytomation Dako Deutschland GmbH, Germany, www.dakogmbh.de
[12] Dianova, Hamburg, Germany
[13] Livingston et al. Cancer Immunol Immunother (2005) 54: 1018-1025
[14] Clausen et al. Mol Immunol(1988) 25: 199-204

Further methods for selection of appropriate microorganisms with cell surface structures which match a human carbohydrate structure are disclosed in the International applications PCT/EP07/009765 and PCT/EP2007/009766 which are incorporated in the present disclosure in their entirety.

According to one embodiment, the microorganism has a cell surface structure which corresponds to a human carbohydrate structure, which is selected from the group of TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, GD3L, Fucosyl GM1, Fucosyl GM1, Lewis-A, Lewis-B, sLac, sialylated type 1 chain, CA 19-9 antigen, CA 72-4 antigen, and CA 50 antigen. The microorganism is thus preferably recognized and bound by at least one binder, as shown in Table 2. Such a test can serve as simple evidence that the microorganism carries a respective cell surface structure.

According to one embodiment, the microorganism has a cell surface structure which corresponds to a human carbohydrate structure which is either TF or Core-1. The Thomsen-Friedenreich antigen (TF) is a known carbohydrate structure which is known as tumor antigen in the state of the art. TF exists in two forms, namely TFalpha and TFbeta which may be bound either on proteins or glycolipids.

Figure 1:
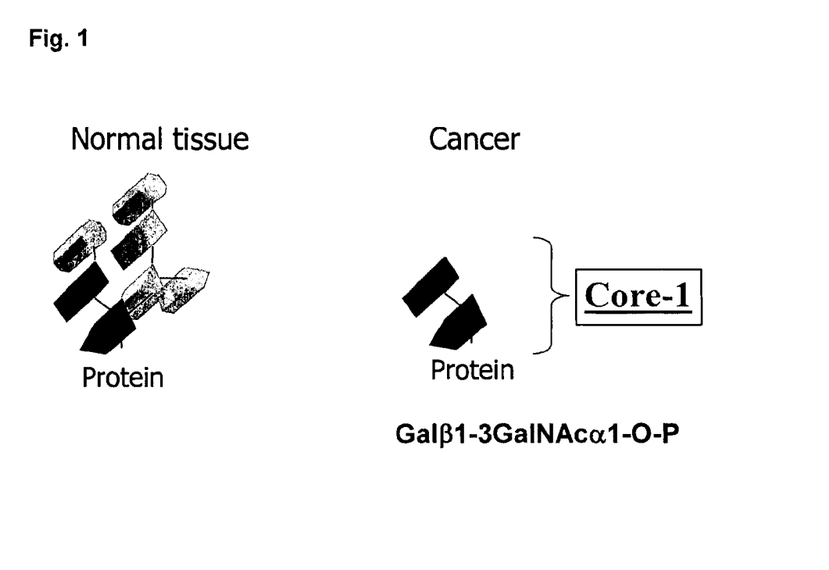
FIG. 1 depicts the Core-1 antigen in healthy tissue versus carcinomas.

Core-1 is the disaccharide Galbeta1-3 GalNAc which is bound as O-glycoside in an alpha-anomeric configuration on the hydroxy amino acids serine or threonine of proteins in cancerous cells. Core-1 corresponds to the TFalpha structure of Thomsen-Friedenreich and is bound exclusively on proteins of tumors. Thus, the terms Core-1 and Thomsen-Friedenreich are not the same because Core-1 corresponds to a substructure of Thomsen Friedenreich. The Core-1 antigen is normally masked by other carbohydrate structures in healthy tissue; it is, however, liberated and thus unmasked in the majority of carcinomas and in some non-epithelial cancer types. The Core-1 antigen is thus a specific pan-carcinoma antigen (see also FIG. 1 for illustration).

Core-1 is accordingly an important tumor antigen. It is expressed on over 60% of the primary intestinal carcinoma and over 90% of liver metastases of intestinal cancer as well as in the majority of the carcinomas of other cancer types, including breast, lung, ovarian, prostate, and other gastrointestinal cancer types, such as, for example, gastric and pancreatic carcinomas. As a result of the wide distribution of this antigen, it is advantageous to provide a microorganism having a cell surface structure corresponding to Core-1. Therefore, according to an embodiment of the present invention, at least one microorganism having at least one cell surface structure corresponding to Core-1 is used for producing a fermented food. Because the fermented food has the respective Core-1 positive microorganism, an immune response against Core-1 can be triggered when the fermented food is consumed so as to realize a certain protective and thus health-promoting effect. This is also true for microorganisms having cell surface structures which match other disease-associated human carbohydrate structures.

According to one embodiment, the microorganism, which has at least one cell surface structure in correspondence to Core-1, is recognized and bound by at least one, preferably two Core-1 specific antibodies, selected from the group comprised of
Nemod-TF1
Nemod-TF2
A78-G/A7
HB-T1
HH8.

Preferably, the binding of the Core-1 specific antibodies is sensitive to periodate, i.e. the binding is reduced by a periodate treatment. Preferably, the microorganism is bound by NEMOD-TF2 or A78-G/A7 and NEMOD-TF1 but not by the antibody A68-B/A11. Such a binding profile is especially advantageous as it corresponds to the binding profile of a human cancer-associated Core-1 structure.

Figure 2:
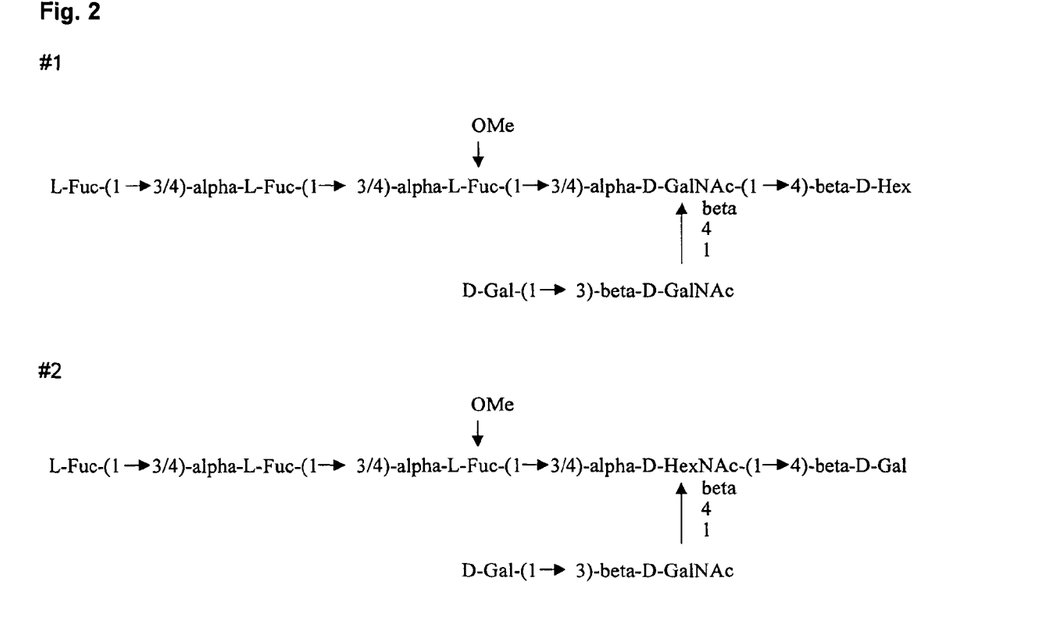
FIG. 2 shows exemplary carbohydrate structures of a microorganism used for production of a fermented food.

According to one embodiment, at least one microorganism is used for production of a fermented food, carrying at least one carbohydrate structure which is selected from the group of carbohydrate structures No. 1, 2, 3, 4 and/or 5 of FIG. 2.

The invention further provides a method of producing a fermented food, wherein the food raw material is combined with a starter culture for fermentation, wherein the method is characterized by adding at least one microorganism of the genus *Bacteroides*. It has been shown that microorganisms of the genus *Bacteroides* positively affect the production and the properties of the fermented food. This was surprising as this genus has not been utilized to date for the production of fermented foods. The fact that microorganisms of the genus *Bacteroides* can be used as processing aid and especially as starter cultures for fermented foods was therefore extremely surprising. The genus *Bacteroides* involves anaerobic, pleomorphic Gram-negative rod-shaped bacteria which belong to the normal flora of the mucous lining of the intestinal tract. More than $10^{11}$ specimens can be found in the large intestine per gram stool. Preferably, the microorganism is selected from the group *Bacteroides fragilis, Bacteroides ovatus, Bacteroides vulgatus, Bacteroides stercoris, Bacteroides eggerthii, Bacteroides uniformis,* and *Bacteroides thetaiotaomicron*. These microorganisms, too, can posses a cell surface structure which corresponds to a human carbohydrate structure.

According to one embodiment, the microorganism is selected from the strains AG6 (DSM 18726), MU1 (DSM 18728) and LH2 (DSM 18727). These were deposited with the DSMZ, Inhoffenstraße 7b, D-38124 Braunschweig, by Glycotope GmbH, Robert-Rössle-Straße 10, D-13125 Berlin, on 20 Oct. 2006. It has been shown that the microorganisms AG6 and MU1 have cell surface structures which correspond to the human Core-1. Furthermore, microorganisms according to the invention can be used which are homologous to AG6 and/or MU1. A microorganism which is homologous to AG6 or MU1 is characterized in that it belongs to the genus *Bacteroides* and bound by at least two Core-1 specific antibodies. Core-1 specific antibodies involve, for example, Nemod-TF1, Nemod-TF2, A78-G/A7, HB-T1, and HH8. Preferably, a homologous microorganism is used in which the binding of the Core-1 specific antibodies is sensitive to periodate. In other words, the binding is reduced by a periodate treatment. Details to the AG6 and MU1 as well as their effects, including detailed experiments are disclosed in the International applications PCT/EP2007/009765 and PCT/EP2007/009766 which are herewith incorporated in the present disclosure in their entirety.

The microorganism according to the invention can be added for starting, during, or after conclusion of the fermentation process. In the event the microorganism is admixed to the already fermented product after fermentation, a starter culture is preferably used in addition in order to initiate the fermentation process. Starter cultures involve microorganisms which are capable of reproduction and are present in pure culture or mixed culture and which are added to the food with the intention to enhance the look, smell, taste and/or shelf life. The following table provides an overview about starter cultures that are known in the state of the art and can be used depending on the fermented food being produced. Of course, this is only a selection; other known starter cultures may also be used. Others were also described here.

TABLE 3

| Group | Genus | Food |
|---|---|---|
| Bacteria | *Lactobacillus* | Cheese, Bread, Sauerkraut, Raw Sausage |
| | *Lactococcus* | Milk, Butter, Cheese |
| | *Leuconostoc* | Butter, Cheese, Wine |
| | *Pediococcus* | Raw Sausage, Vegetables, Soy Sauce |
| | *Streptococcus* | Yogurt, Cheese |
| | *Micrococcus* | Raw Sausage |
| | *Staphylococcus* | Raw Sausage |
| Yeast | *Saccharomyces* | Alcoholic Beverages, Bread, Soy Sauce |
| | *Candida* | Kefir, Raw Sausage |
| Molds | *Penicillium* | Cheese, Raw Sausage |
| | *Aspergillus* | Soy Sauce, Uncooked Ham |

In particular the microorganisms *streptococcus thermophilus* and *lactobacillus bulgaricus* can be used for producing yogurt products. However, other starter cultures known in the state of the art can be used to initiate the fermentation. The microorganisms according to the invention may be added according to one embodiment at the end of the fermentation process, similar to probiotic products. As opposed to probiotic products, the microorganisms according to the invention are, however, present in the fermented finished food preferably (depending on the used microorganism) in a form which is incapable to reproduce. This may be realized for example through irradiation of the microorganisms or heating. Preferably, the microorganisms are killed. This may involve either a treatment of the microorganisms before being added to the product or the fermented food to which the microorganisms have been added is accordingly treated. As the microorganisms, regardless whether they are incapable to reproduce or killed, still retain the cell surface structure which corresponds to a human carbohydrate structure, the microorganisms according to the invention can still provide the health-promoting effect in the finished food product.

The microorganisms used in accordance with the invention may further be used as starter cultures because they surprisingly have the ability to initiate the fermentation process. This was especially surprising for microorganisms of the genus *Bacteroides* (see above) and especially AG6 and MU1 as well as homologues thereof because they have not been used as starter culture for production of a fermented food heretofore. The microorganisms according to the invention may hereby represent the single starter culture. It is, however, also possible to use the microorganisms according to the invention in combination with other starter cultures. This may be beneficial in order to influence the taste, degree of acidification and/or consistency of the fermented product and to alter it as requested. The metabolic activity of the bacterial cultures produces volatile aromatic compounds, such as, for example, acetic acid, diacetyl aldehyde and acetal aldehyde, which in combination with the acidity contribute to the unique acidic or tart aromatic characteristic of the product. Mixing various starter cultures allows respective adjustment of the desired characteristics. Of course, the present invention covers also variants which use the microorganisms according to the invention as starter culture (optionally in combination with other starter cultures) as well as additive to the fermented product. Such an embodiment may be advantageous in order to adjust or increase for example the quantity of microorganisms present in the fermented product.

In the event the microorganisms according to the invention are used as starter cultures, the fermentation product is again preferably treated such that the microorganisms are contained in the fermented finished food in a form that renders them incapable to reproduce. This involves killing of the microorganisms, for example through pasteurization, ultra-heat treatment, or sterilization.

The method according to the invention allows production of most varied foodstuffs. The latter may be based on plant sources such as, for example, beer, wine, sour dough or yeast dough or soy products. They may also be of animal source, in particular milk and/or meat products. A non-limiting exemplary list of products producible by the method according to the invention includes fermented milk products such as sour whey, curdled milk/sour milk, gelatin, cream cheese, soft cheese, cut cheese, hard cheese, processed cheese, quark, cheese from curdled milk, cooked cheese, kefir, ymer, avran, molasses, yogurt, fruit yogurt, sweet whey, whey butter, fresh cheese, mozzarella, feta cheese, whey powder, sour cream, crème fraiche, mascarpone, smetana, sour cream, sour cream butter, butter, butter oil, semi-fat butter, mildly soured butter, raw sausages such as, for example, salami or salty meat, cacao, coffee, sour dough and soured vegetables such as, for example, sauerkraut. The food raw material is selected in accordance with the fermented food product to be produced.

The microorganisms according to the invention may be used as starter culture either alone or in combination with common starter cultures for producing fermented meat products. Normally, starter cultures are used in particular when ripening of raw sausage is involved. They cause a reduction of the pH value and convert the meat-intrinsic and added sugar ingredients into organic acids. Furthermore, they cause a solidification of the meat protein. Lowering of the pH value causes a decrease in the water absorptive capacity. The decrease in the pH value also has a preserving effect. In particular lactic acid bacteria, such as, for example, homofermative representatives of the genera *lactobacillus* and *pediococcus* are appropriate, which can be used as starter cultures instead of or in combination with the microorganisms according to the invention. Also in this case, it is again possible to add the microorganisms according to the invention after fermentation as a kind of probiotic addition. However, the microorganisms are present in the finished product (depending on the used microorganism) preferably in a form incapable of reproduction and preferably in a killed form (see above). This is true in particular when the involved microorganism is *Bacteroides*. To shorten the ripening time and to realize a particular aroma, lactic acid bacteria strains may be used which have a high production of lactic acid. For influencing the aroma, for example microorganisms with a particular protease and lipase activity can be used, such as in particular *staphylococcus, micrococcus*, but also molds.

The method may include at least one of the following method steps:

Inoculating the food raw material with a starter culture, containing at least one microorganism having at least one cell surface structure matching a human carbohydrate structure. The raw material may, for example, be inoculated with at least about $1 \times 10^6$, preferably about 1 to $7 \times 10^9$ microorganisms per ml raw material. Corresponding quantities have been proven beneficial when inoculating milk, especially with cultures of *Bacteroides* selected from the group *Bacteroides fragilis, Bacteroides ovatus, Bacteroides vulgatus, Bacteroides stercoris, Bacteroides eggerthii, Bacteroides uniformis*, and *Bacteroides thetaiotaomicron* as well as in particular AG6 or MU1. However, the amounts may vary depending on the raw material and desired end product.

Incubation of the inoculated food raw material under anaerobic conditions. This procedure is especially beneficial when using anaerobic bacteria as starter cultures, such as, for example, *Bacteroides* (see supra for the groups to be used and especially AG6 and MU1). The incubation may, for example, take place under a $N_2$, $CO_2$ and/or $H_2$ atmosphere.

Incubation of the inoculated food raw material at about 30 to 50° C. The temperature may again vary in dependence on the used microorganism as starter culture, raw material, and desired end product. Temperatures between 35 and 40° C. have proven especially beneficial for incubation of cultures of *Bacteroides*, in particular during fermentation of milk for producing fermented milk products such as, for example, yogurt.

According to one embodiment, sugar, preferably glucose, is added to milk, preferably at a concentration of at least 3 g/l, preferably at least 5 g/l.

According to one embodiment, the fermented food involves a milk product. This may be yogurt and in particular yogurt drink. Raw material may include any milk product or milk-like product, such as whole milk or low-fat milk, skim milk, condensed milk, dry low-fat milk, lactose, or cream. Milk is hereby to be understood to relate to a milk-like secretion which is obtained through milking any animal such as, for example, cows, sheep, goats, buffalos, or camels. In addition, the invention includes the possibility to produce the milk or the milk-like product through suspension of low-fat milk powder and/or full-fat milk powders in an aqueous medium. The term fermented milk product is to be understood as relating to any milk product, including a milk raw material as described above and which undergoes any fermentation type. Examples of fermented milk products which can be produced by the method according to the invention are listed above. For production of the fermented milk product, a milk raw material as defined above is made available. The milk raw material may be pretreated through pasteurization, sterilization, heat treatment, or any other suitable way in order to kill possible germs. Pasteurization and sterilization methods are known in the state of the art and require no description. The milk raw material is combined for fermentation with a starter culture which may contain the microorganism according to the invention. In the event the microorganism according to the invention is added later only as additive or in combination with other starter cultures for fermentation, an appropriate starter culture is selected in dependence on the product to be produced. Appropriate starter cultures are known in the state of the art.

The dosages of starter culture to be added and the incubation temperatures vary in dependence for example on the starter culture and the milk raw material which are used and on the desired end product. The milk raw material, including starter culture and optionally further additives, are caused to ferment under conditions that are generally known in the art. Examples of fermentation conditions which may vary depending on the used microorganism as starter culture include temperatures between 20-50°, preferably 35-46°, for at least three hours. Incubation is preferably implemented long enough until the desired pH value is reached. The latter is preferably in the acidic range, preferably below pH 6 or pH 5. In the event of producing a product that is low in lactose, lactase may be added to the raw material to hydrolyze lactose.

The method according to the invention allows production in particular of fermented milk products such as, for example, yogurts, in particular yogurt drink. Preferably, the production is realized with the use of a *Bacteroides* microorganism which is preferably selected from the group *Bacteroides fragilis*, *Bacteroides ovatus*, *Bacteroides vulgatus*, *Bacteroides stercoris*, *Bacteroides eggerthii*, *Bacteroides uniformis*, and *Bacteroides thetaiotaomicron*. These may or may not have a human carbohydrate structure as described above.

Thickening of milk begins at a pH value of about 5.5 and ends, depending on the culture and product, e.g. for a fermented milk product such as, for example, a yogurt, at a pH value between 3.8 and 4.6 (pH of milk: approx. 6.5). When using the bacterial strains AG6 and/or MU1, pH values of below 5 are reached. However, products having a pH value of 5.5 may be used already as yogurt drink. There is also the possibility to discontinue fermentation, when a particular pH value has been reached. The pH value can thus be varied by the added starter cultures and the length of the fermentation process.

The viscosity of milk is about 1 mps-1. Semisolid yogurt has a viscosity of above 100 mps-1, e.g. of 150 mps-1. A yogurt drink typically has a viscosity of below 120 mps-1. A yogurt drink which contains in accordance with the invention the microorganisms AG6 and/or MU1, may have a viscosity of, for example, at least 5-10 mps-1. The viscosity is also dependent on the presence of fruits.

As stated, the acidic content and the type of acid can be varied through use of various starter cultures. The bacterial strains listed in the following table 4 may be used for production of yogurt, for example; they produce the acids as listed hereinafter.

TABLE 4

| Designation | Growth Temperature (Optimum) | Metabolic Product |
|---|---|---|
| *Lactococcus lactis* ssp. *lactis* (previously *Streptococcus lactis*) | 20-30° C. | Lactic Acid |
| *Lactoc. lactis* ssp. diacetilactis (previously *Strept.* diacetilactis) | 20-25° C. | Lactic Acid, Diacetyl, $CO_2$ |
| *Lactoc. lactis* ssp. *cremoris* (previously *Strept. cremoris* | 20-30° C. | Lactic Acid |
| *Leuconostoc*-types (Betacoccus) In particular appropriate for production of quark and buttermilk | 20-25° C. | Lactic Acid, Diacetyl, $CO_2$, Acetic Acid, Alcohol |
| *Lactobacillus delbrückii* ssp. *bulgaricus* (previously *Lactobacillus bulgaricus*) In particular appropriate for production of yogurt | 40-45° C. | Lactic Acid, Acetaldehyde |
| *Streptococcus thermophilus* In particular appropriate for production of yogurt | 35-40° C. | Lactic Acid |

Two types of lactic acids are realized during fermentation: the dextrorotatory L(+) lactic acid and the levorotatory D(−) lactic acid. Both types of lactic acid are chemically virtually the same, they differ however with respect to their physical properties. When irradiating lactic acid with polarized light, dextrorotatory lactic acid "rotates" the light to the right, levorotatory accordingly to the left. Which lactic acids are contained in fermented food depends predominantly on the bacterial culture used for production. *Streptococcus* bacteria and bifidobacteria form almost exclusively dextrorotatory, *lactobacillus bulgaricus* almost exclusively levorotatory lactic acid, and *lactobacillus acidophilus* forms both types of lactic acid approximately each by half. While the bacteria of buttermilk, sour milk, and sour cream form dextrorotatory lactic acid by about 90 percent, typical yogurts contain both types at different ratios. Milder yogurt contains predominantly dextrorotatory lactic acid.

The dextrorotatory lactic acid is produced in the human body and therefore easily and rapidly degraded by the organism. The levorotatory lactic acid is foreign to the body and thus is metabolized slightly slower. This normally does not adversely affect the health of healthy humans. Only babies should not intake levorotatory lactic acid during the first months because their metabolism has not yet fully matured.

In one embodiment, the *Bacteroides* cultures are produced using a bioreactor. For example, the medium is inoculated with a pre-culture in an amount of 0.2 to 10%, preferably about 2%. The fermentation with the *Bacteroides* culture may proceed over night under anaerobic conditions at a temperature of between 35 and 42° C., preferably about 37° C., at a pH-value between 5 and 9, preferably about 7.

Preferably, at the end of the fermentation, when the glucose is completely or nearly completely used up, a feeding phase is started. For this, further medium (feed-medium) is continuously added during a time of, for example, 3 to 10 hours, preferably 4 hours. The addition rate is preferably between 1 and 20% of the fermentation volume per hour, more preferably about 10% per hour. The feed-medium is preferably composed as follows:

10 g/l glucose and 10 g/l yeast extract plus optionally one or more additives selected from the following list:
Cysteine
Glucose
Pyruvate
Yeast extract
Methionine
Galactose
NaCl The remaining process proceeds until the end of the milk fermentation as is also described herein.

The product may be thickened after pasteurization. For this, different common methods can be used. For example, the thickening can be effected by ultrafiltration.

The product which preferably is thickened may be spray-dryed, resulting in a fine powder. Probiotic bacterial cultures or other additives may be added to the obtained powder before it is preferably encapsulated to provide a capsule.

The present invention further provides for a fermented food which can be produced in accordance with the described method.

Furthermore, a fermented food is provided which has at least one *Bacteroides* microorganism. Preferably the microorganism is selected from the group *Bacteroides fragilis, Bacteroides ovatus, Bacteroides vulgatus, Bacteroides stercoris, Bacteroides eggerthii, Bacteroides uniformis,* and *Bacteroides thetaiotaomicron*.

Furthermore, a fermented food is provided which contains at least one microorganism having at least a cell surface structure which corresponds to a human carbohydrate structure. Appropriate microorganisms are described above and in the claims in detail. We refer to the above explanations. Preferably, the microorganism is a Core-1 positive microorganism, especially AG6, MU1, or a homologous microorganism. The used microorganism preferably carries a carbohydrate structure which is selected from the group of the carbohydrate structures no. 1, 2, 3, 4, and/or 5 of FIG. 2.

The food according to the invention may contain in addition to the microorganism according to the invention one or more common starter cultures. According to one embodiment, the microorganism according to the invention is, however, used exclusively as starter culture.

According to one embodiment, the fermented food has at least $10^6$ units of the microorganism according to the invention.

According to one embodiment, the fermented food contains the microorganism according to the invention in a form incapable to reproduce, e.g. in killed state. This embodiment is especially advantageous when using a *Bacteroides* microorganism.

Details have been described above in connection with the method, and we make reference to the respective disclosure.

In accordance with the invention, a processing aid is further provided for production of fermented foods, the processing aid being characterized by at least one microorganism having at least one cell surface structure which corresponds to a human carbohydrate structure. Processing aid is to be understood as relating to materials which in itself are not an ingredient that is consumed as food but are used for technological reasons during treatment and processing of foods and may leave unintended, technically unavoidable residues or decomposition or reaction products of residues in amounts that are harmless from a health point of view for the consumer of certain foods and which have no technological effect on this food (processing aids). Preferably, the processing aid is a starter culture. Appropriate microorganisms are described above and in the claims in detail. We refer to the respective disclosure. The same is true for the use of *Bacteroides*.

EXAMPLES

The method according to the invention will now be described in detail with reference to examples.

1. Example 1

An exemplary method for production of a yogurt is described hereinafter. For production of a yogurt, milk is "thickened", i.e. a so-called gelatin is formed. This is also referred to as a semisolid yogurt. The milk required for the production of the yogurt is adjusted to the desired fat content, the possible excess amount of milk fat may, if desired, be separated through centrifugation. The consistence of the yogurt may be varied for example through addition of milk powder because the content of dry mass can be increased in this manner. The adjusted milk then undergoes a heating operation, for example pasteurization or ultra-heat treatment so that all unwanted bacteria, contained in the raw material, are killed. The milk is preferably further homogenized (comminution of the fatty globes contained in the milk so as to prevent creaming up). Then, the milk is cooled down to about 30-50°, preferably 35 to 41°, and moved to a storage tank. The starter cultures are added in this storage tank; a stirrer is used to provide a thorough mixing, and then the milk is allowed to rest in the storage tank while the agitator is turned off. As a result, the so-called fermentation now begins, i.e. the cultures begin to work. The milk sugar contained in the milk is converted through fermentation into lactic acid. This lactic acid in turn causes the milk proteins to agglomerate and a gelatin is formed. During this time period, aroma is also formed which predominantly is comprised of the metabolic products of the used starter cultures and accordingly can be varied through combination of different starter cultures. Examples of common metabolic products include diacetyl, acetaldehyde, and various acids. After the desired pH value of typically below 5 has been reached, it is again stirred so that the further acidification is interrupted. The yogurt mass is cooled and made available for the production. The fermentation takes normally more than 3 hours, typically between 6 and 25 hours, depending on the used bacterial cultures and the fermentation temperature. The process may also be operated longer.

In the event, a fruit yogurt should be produced, respective fruit ingredients may also be added. The respectively finished yogurt can then be poured into cups.

In accordance with the invention, the microorganisms, having a cell surface structure which corresponds to a human carbohydrate structure, and/or microorganisms of the genus *Bacteroides* can be used as processing aid, for example as starter culture.

2. Example 2

The microorganism AG6 was used.

The redox potential of milk is lowered to below +10 mV through incubation overnight under anaerobic conditions or through heating to a high temperature of 95° C. Glucose in an amount of 2.5-20 g/l, preferably 5 g/l is added to the milk. The milk is inoculated with $2.5 \times 10^9$-$7 \times 10^9$ bacteria/ml milk (preferably $5 \times 10^9$ bacteria/ml milk). The inoculated milk is incubated under anaerobic conditions or under a $CO_2$ atmosphere at 37-41° C. (preferably at approx. 38-39° C.). The inoculated milk has a viscosity of approx. 1.5-2.5 mps-1.

After about 10-20 hours of incubation time, the milk has a viscosity of approx. 5-50 mps-1. Higher viscosities may be varied for example through addition of starch (for example milk powder) and/or through inoculation of a further starter culture. In this way, semisolid yogurt products can also be produced.

3. Example 3

In this example, a *Bacteroides* culture was used which has been inoculated the preceding day with 5% in WC (Wilkings Chalgren) medium and incubated overnight under anaerobic conditions at 37° C. The bacteria were concentrated by centrifugation and subsequently activated. The activation has been realized through reception of the pellet in fresh medium which has been degassed by anaerobic bags and incubation under anaerobic conditions at 37° C. for 2 hours. After the activation phase, the bacteria were concentrated again and absorbed in milk. This procedure has been proven beneficial, when using *Bacteroides* cultures.

Figure 3:
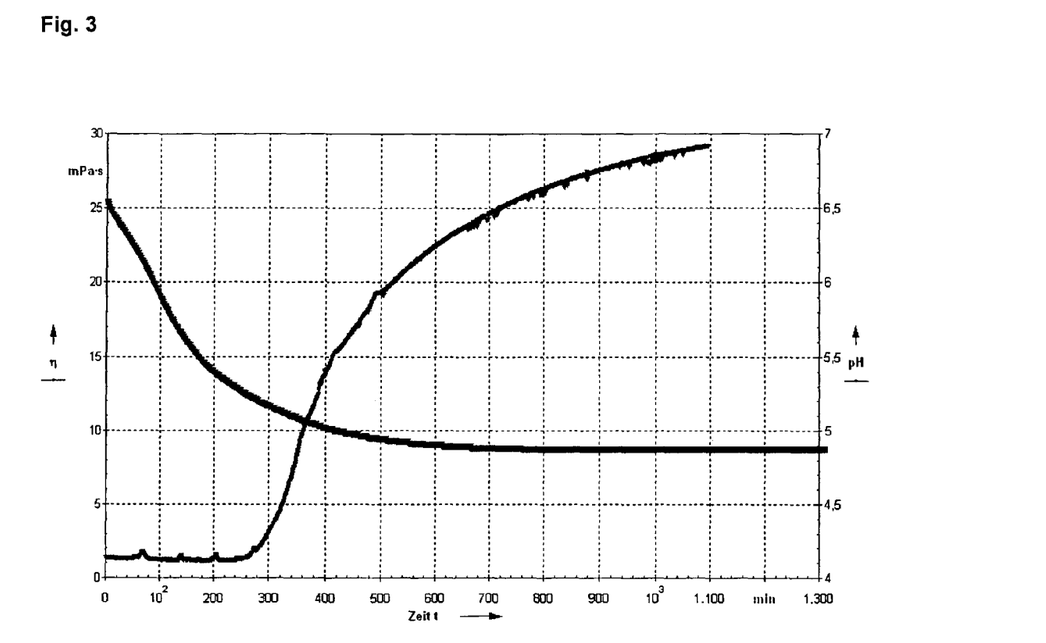
FIG. 3 shows the viscosity and pH developments of milk inoculated under particular conditions, during the fermentation process.

The milk to be fermented was degassed overnight by means of anaerobic bags. At the start of the experiment, the degassed milk was inoculated with a bacterial amount of 4.0*109 c/ml. In addition, at the start of the experiment the milk was adjusted to a glucose concentration of 5 g/L by addition of a glucose solution FIG. 3 shows the viscosity and pH developments of the inoculated milk during the fermentation process. The pH reached a value of 4.85 and the viscosity a value above 25 mps-1, resulting in the development of a viscous, thickened and creamy product.

These conditions led to the development of a viscous, fermented milk product when using a *Bacteroides* starter culture as sole starter culture.

4. Example 4

In this example, a *Bacteroides* culture was used which has been inoculated the preceding day with 2.5% in WC medium and incubated overnight under anaerobic conditions at 37° C. The bacteria were concentrated by centrifugation. The pellet was directly absorbed into degassed milk.

The milk to be fermented was also degassed overnight by means of anaerobic bags. At the start of the experiment, the degassed milk was inoculated with a bacterial amount of 6.0*109 c/ml. In addition, at the start of the experiment the milk was adjusted to a glucose concentration of 5 g/l by addition of a glucose solution.

Figure 4:
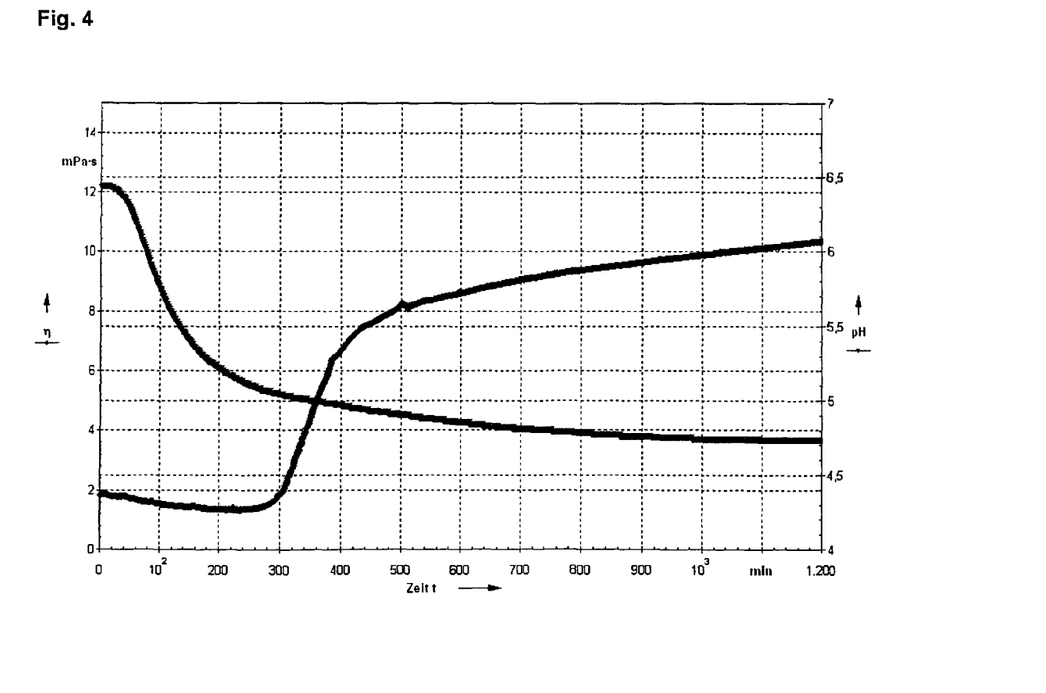
FIG. 4 shows the viscosity and pH developments of milk inoculated under particular conditions, during the fermentation process.

FIG. 4 shows the viscosity and pH developments of the inoculated milk during the fermentation process. The pH reached a value of 4.75 and the viscosity a value of 10 mps-1. At the end of the experiment, the product was viscous, thickened and creamy.

Under the described conditions, the use of a *Bacteroides* cultures results in a viscous milk product.

An important condition for a successful fermentation is a basically intense metabolic activity of the bacteria. For this purpose, the bacteria are preferably in the exponential phase. As an alternative, the bacteria can be reactivated through incubation in fresh medium.

The acidification kinetics was identified as most important factor for a successful milk fermentation.

The invention claimed is:

1. A method of producing a fermented food, wherein a food raw material is combined with a starter culture for fermentation, comprising the steps of:
   adding at least one microorganism of the genus *Bacteroides* as starter culture;
   incubating the inoculated food raw material under anaerobic conditions at approximately 20° C. to 50° C. whereby a fermented food is produced; and
   pasteurizing or sterilizing the fermented product.

2. The method according to claim 1, wherein the at least one microorganism added comprises at least one of the following features:
   a. the microorganism is chosen from *Bacteroides ovatus, Bacteroides vulgatus, Bacteroides stercoris, Bacteroides eggerthii, Bacteroides uniformis*, and *Bacteroides thetaiotaomicron*; and/or
   b. the microorganism has at least one cell surface structure corresponding to Core-1 and is bound by at least one-Core-1 specific antibody chosen from
   Nemod-TF1,
   Nemod-TF2,
   A78-G/A7,
   HB-T1, and
   HH8; and/or
   c. the microorganism is bound by NEMOD-TF2 or A78-G/A7 and NEMOD-TF1, but not by the antibody A68-B/A11; and/or
   d. the microorganism is chosen from AG6 (DSM 18726), MU1 (DSM 18728) and/or AG6 or MU1 homologous microorganisms, wherein the microorganism belongs to the genus *Bacteroides* and is bound by at least two Core-1 specific antibodies chosen from
   Nemod-TF1,
   Nemod-TF2,
   A78-G/A7,
   HB-T1, and
   HH8.

3. The method according to claim 1, wherein the microorganism of the genus *Bacteroides* is used as sole starter culture or in combination with at least one further starter culture.

4. The method according to claim 1, wherein the microorganism of the genus *Bacteroides* is present in the finished food in a form incapable to reproduce.

5. The method according to claim 1, comprising at least one of the following method steps:
   concentrating the microorganisms and adding the concentrated or palletized microorganisms in fresh medium for activation;
   inoculating the food raw material with a starter culture, containing at least one microorganism chosen from *Bacteroides fragilis, Bacteroides ovatus, Bacteroides vulgatus, Bacteroides stercoris, Bacteroides eggerthii, Bacteroides uniformis*, and *Bacteroides thetaiotaomicron;*
   inoculating the food raw material with an activated starter culture;
   inoculating the food raw material through use of microorganisms which are in the exponential phase; and
   adding at least one sugar in an amount of at least 3 g/l.

6. The method according to claim 1, wherein a feeding phase is started at the end of fermentation, wherein said feeding phase has one or more of the following characteristics:
   a. the feed-medium is added during a time period of 3 to 10 hours; and/or b. the addition rate of the feed-medium is between 1 and 20% of the fermentation volume per hour; and/or c. the feed medium comprises 5 to 15 g/l glucose and 5 to 15 g/l yeast extract; and/or d. the feed medium comprises one or more additives chosen from cysteine, glucose, pyruvate, yeast extract, methionine, galactose and NaCl.

7. The method according to claim 1, wherein the food raw material is milk.

8. A fermented food, produced by the method according to claim 1.

9. The fermented food according to claim 8, comprising at least one of the following features:

at least one further microorganism different from the at least one microorganism of the genus *Bacteroides* is used as starter culture; and/or at least one microorganism of the genus *Bacteroides* in a form incapable to reproduce; and/or at least $10^6$ microorganisms of the genus *Bacteroides* per daily amount of consumption.

10. A method of producing a fermented food, wherein a food raw material is combined with a starter culture for fermentation, comprising the steps of:

adding at least one microorganism of the genus *Bacteroides* as starter culture;

incubating the inoculated food raw material under anaerobic conditions;

incubating the inoculated food raw material at approximately 20 to 50° C.; and wherein the microorganism of the genus *Bacteroides* is present in the finished food in a form incapable to reproduce.

* * * * *

UNITED STATES PATENT AND TRADEMARK OFFICE
CERTIFICATE OF CORRECTION

| | | |
|---|---|---|
| PATENT NO. | : 8,741,365 B2 | Page 1 of 1 |
| APPLICATION NO. | : 12/991827 | |
| DATED | : June 3, 2014 | |
| INVENTOR(S) | : Goletz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 587 days.

Signed and Sealed this
Twenty-eighth Day of July, 2015

Michelle K. Lee
*Director of the United States Patent and Trademark Office*